United States Patent [19]

Urano

[11] 4,254,339

[45] Mar. 3, 1981

[54] METHOD FOR THE FLUORIMETRIC QUANTITATIVE DETERMINATION OF $SO_2$ IN GASES AND APPARATUS THEREFOR

[75] Inventor: Yoriyuki Urano, Shiga, Japan

[73] Assignee: Yanagimoto Seisakusho Co. Ltd., Kyoto, Japan

[21] Appl. No.: 917,845

[22] Filed: Jun. 22, 1978

[30] Foreign Application Priority Data

Jun. 29, 1977 [JP] Japan ............................... 52-78547
Jul. 22, 1977 [JP] Japan ............................... 52-88527

[51] Int. Cl.$^3$ ...................... G01N 21/38; G01J 1/58
[52] U.S. Cl. ............................. 250/459; 250/461 R
[58] Field of Search ............... 250/372, 373, 461 R, 250/458, 459, 365

[56] References Cited

U.S. PATENT DOCUMENTS 3,612,866 10/1971 Stevens .............................. 250/373

OTHER PUBLICATIONS

Schwarz et al., "Fluorescence Detection of Nitric Oxide in Oxygen", Anal. Chem., 47, No. 4, 4-75, pp. 703-707.

Schwarz et al., "Fluorescence Measurements of Benzene, Naphthalene, Anthracene, Pyrene, Fluoranthene, and Benzo[e]pyrene in Water", Anal. Chem., 48, No. 3, 3-76, pp. 524-528.

Schwarz et al., "Fluorescence Detection of Sulfur Dioxide in Air at the Parts per Billion Level", Anal. Chem., 46, No. 8, 7-74, pp. 1024-1028.

*Primary Examiner*—Alfred E. Smith
*Assistant Examiner*—Carolyn E. Fjelds

[57] ABSTRACT

A fluorimetric method for the quantitative determination of $SO_2$ in gas provides a stable measuring base. It consists in lowering the background values in terms of $SO_2$ concentrations to about 2/10 of one ppm by increasing the oxygen concentration in a reference gas to at least 2%. This is effected by adding to this reference gas an $O_2$-containing stream or an ozone-containing stream. When the ozone-oxygen mixture is used the increase in $O_2$ concentration need not be higher than 0.5–1.0% (instead of at least 2%) to achieve the same background $SO_2$ reduction (see FIG. 4).

16 Claims, 6 Drawing Figures

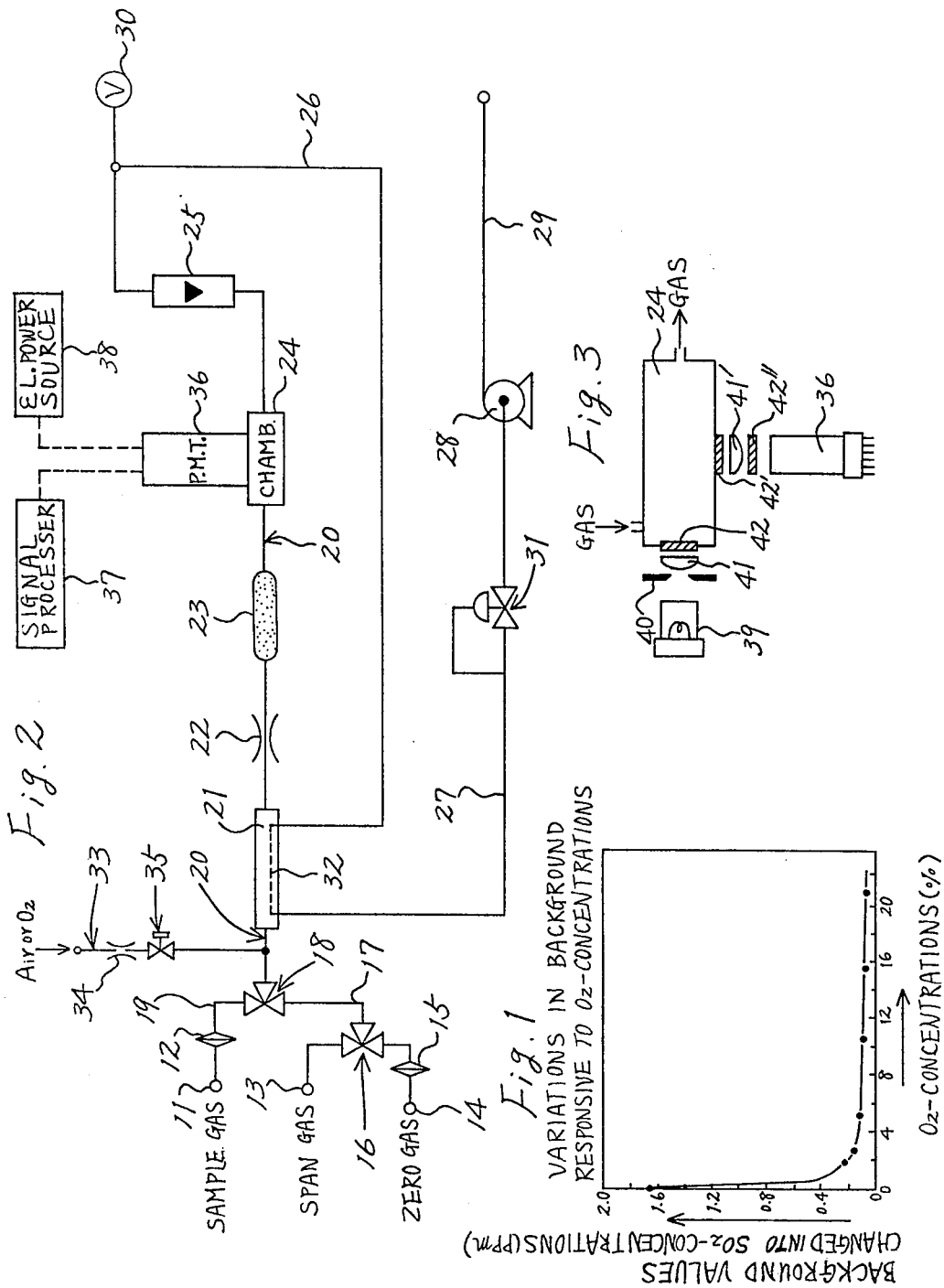

METHOD FOR THE FLUORIMETRIC QUANTITATIVE DETERMINATION OF SO₂ IN GASES AND APPARATUS THEREFOR

BACKGROUND OF THE INVENTION

The present invention relates to a fluorometric method and instrument for determining $SO_2$ concentration, employing a novel base stabilizing mechanism.

The $SO_2$ molecule has three absorption wavelength ranges in the ultraviolet region, and if excited by ultraviolet rays within any of these wavelength ranges, it generates fluorescent ultraviolet rays. More particularly, a first absorption wavelength range is 340–390 nm, a second is 250–320 nm and a third is 190–230 nm. However, it has been found that in the first wavelength range, the absorption of ultraviolet rays by $SO_2$ molecules is very weak and that in the second wavelength range, the quenching or masking effect of the nitrogen and $O_2$ gas in the atmosphere on the absorption and excitation of $SO_2$ molecules is so high that ultraviolet rays in said second wavelength range cannot be used for satisfactory measurements of $SO_2$ concentration.

The present invention is concerned with the measurement of $SO_2$ concentration by using said third wavelength range.

In the third wavelength range, although the background phenomena interfering with the $SO_2$ excitation are not as strong as in said second wavelength range, still the background offers variations in the zero base indications on a quantitative scale, said variations corresponding to about 0.1–1.6 ppm in terms of $SO_2$ concentration. To indicate quantitatively only the $SO_2$ presence, the zero base must be made by a so-called zero gas which ordinarily consists of highly pure $N_2$, an inert gas comprising any rare gas, or air having $SO_2$ removed therefrom. In cases where a span gas is used to establish the span base of indications, this span gas should comprise the same component as said zero gas to dilute a known amount of $SO_2$ to provide the span concentration thereof.

SUMMARY OF THE INVENTION

I have investigated the base stability of indications relative to the substance of the zero gas. As a result, it has been ascertained that whereas a zero gas comprising $N_2$ or rare gases has a relatively high background level and is unstable, air having $SO_2$ removed therefrom has a low background level and is stable. If the cause of such different backgrounds is sought with particular reference to $N_2$ and air backgrounds, it is believed to be due to a substantial component of air other than $N_2$ which accounts for a large part of air and it is due to the presence or absence of oxygen as the substantial component. This has been confirmed by varying the concentration of oxygen gas within a zero gas consisting largely of $N_2$. Further, the critical point of oxygen concentration capable of keeping the background to a low and stable level has been confirmed.

Accordingly, an object of the present invention is to provide a method and instrument, based on said discovery, for fluorometrically determining $SO_2$ concentration, capable of establishing a stable measuring base by supplying the zero gas or gas with a sufficient amount of oxygen to develop the quenching or masking effect on the background.

Another object of the invention is to provide a method and instrument for fluorometrically determining $SO_2$ concentration, capable of establishing a stabler measuring base by mixing the zero gas or the like and also a sample gas with ozone, which has a greater background suppressing effect than oxygen. This is because it is believed that the background suppressing effect, even in the case of said oxygen supply, is due largely to some ozone which is produced by the excitation of oxygen in the fluorescent chamber.

These and other objects and advantages of the invention will become more apparent from the following detailed description of the invention given with reference to the accompanying drawings.

BRIEF DESCRIPTION OF THE DRAWINGS

FIG. 1 is a graph showing an $O_2$ concentration-background characteristic;

FIG. 2 is a diagram showing the flow outline of an embodiment of the invention employing a flow system for supplying the reference gas with $O_2$;

FIG. 3 is a sectional view showing the optical system of a fluorescent chamber;

DETAILED DESCRIPTION OF THE INVENTION

Figure 4:
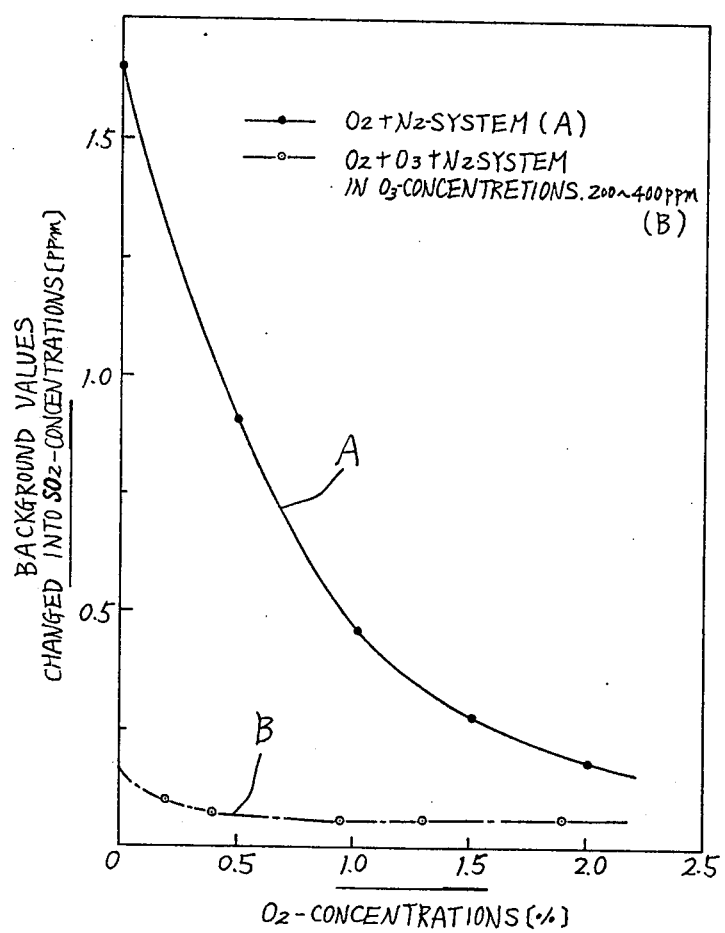
FIG. 4 is a graph showing an $O_2$–$O_3$ systemic concentration-background characteristic in comparison with $O_2$ concentration.

Referring to FIG. 1, there is shown a graph obtained by determining the relationship between the mixing ratio of $O_2$ to highly pure $N_2$ gas (99.99% or above) and the background value calculated in terms of $SO_2$ concentration to be measured.

According to this graph, the background value within the $O_2$ concentration range of about 0–1% falls very sharply from about 1.6 ppm, where $O_2$ is not mixed in, to 0.3 ppm, it being seen that beyond the critical range of $O_2$ concentration of 1–3%, the background value decreases very gently or almost horizontally to below about 0.15 ppm. As a result, it is clear that in the case of measuring the concentration of $SO_2$ within combustion exhaust gases or the like still containing at least a few percents of $O_2$, the use of highly pure $N_2$ gas or rare gases directly as the zero gas would lead to a significant erroneous measurement. Particularly, in the process of supplying the zero gas to the fluorescent cell, the leakage of a very small amount of air (and hence $O_2$) into such an inert gas is unavoidable, thus making the base extremely unstable. The same may be said of a sample gas containing as little as less than 2% $O_2$.

The reason why the background value is affected by the $O_2$ concentration in a measured gas is not fully clear. However, in view of the experimental observation that a sharp drop in background value occurs in the range of very small $O_2$ concentrations, my proposed theory of the mechanism involved may be expressed as follows:

The $O_2$ gas which absorbs wavelengths (190–201 nm) in proximity to the irradiated ultraviolet rays would act on trace amounts of background components (e.g., volatile hydrocarbons from the optical paint on the walls within the fluorescent chamber) to quench the luminescence thereof or absorb any scattered or straying light rays due to the irradiation of ultraviolet rays, while the $O_2$ gas thereby energized would itself become stable in a state in which the rate of energy radiation at the wavelength to be photoelectrically detected is small.

In a first embodiment of the invention, based on the above concept, the $O_2$ concentration of 2% which may define the unstable sharp range from the stable low level range in the background curve shown in FIG. 1 is used as the lower limit of $O_2$ concentration for the zero gas or the like. The principal component of the zero gas or the like is mixed with oxygen so as to attain the aforesaid $O_2$ concentration of about 2% and is then fed into a fluorescent cell, thereby setting the zero base or span level for measured values.

This embodiment is also intended to add $O_2$ to a sample gas of an object to be measured, if desired, in order to provide for the stability of the background.

Referring to FIG. 2, there is shown a flow system in the embodiment of the invention described above. In FIG. 2 the reference numeral 11 designates a sample gas inlet; 12 designates a filter for sample gas; 13 designates a span gas inlet; 14 designates a zero gas inlet; and 15 designates a filter for zero gas. Conduits extending from the span gas inlet 13 and zero gas inlet 14 are selectively connected to a conduit 17 at a cock 16, with the end of conduit 17 being coupled to a cock 18 where the conduit and another conduit 19 extending from the gas inlet 11 are alternatively connected to a measuring conduit 20. The measuring conduit 20, starting from the portion directed to the cock 18 is inserted therein by a permeation wet remover 21, a capillary 22, a hydrocarbon cutter 23, a fluorescent chamber 24 and a flowmeter 25, in the order mentioned. A measured gas passed through the flowmeter 25 is sucked through vacuum conduits 26 and 27 to a pump 28, and then discharged through an exhaust channel 29. The series of suction conduits 26 and 27 are provided with a vacuum gauge 30 and a vacuum regulator 31, respectively, and are connected together by the vacuum channel 32 defined in the permeation wet remover 21.

An air or oxygen compensation line 33 meets the measuring conduit 20 between the cock 18 and the permeation wet remover 21. The line 33 has a capillary 34 and a valve 35 placed therein so that $O_2$ can be added to the zero gas or the like at a desired rate according to the invention.

The intensity of luminescence from gas molecules in the fluorescent chamber 24 is detected by a photomultiplier 36. The detected signal from the photomultiplier 36 is fed to a signal processing circuit 37. The numeral 38 designates a power source for the photomultiplier 36.

Referring to FIG. 3, there is shown a conventional optical arrangement including the photomultiplier 36 and parts provided for the emission of ultraviolet rays to the fluorescent chamber 24. As an excitation light source, in this case, a Xe discharge tube 39 is used. The tube 39 is pulsed to radiate the light with a period of 100 milliseconds and a lighting duration of 1 microsecond. The light irradiates the chamber 24 through a slit 40, a lens 41 and a filter 42 which is used to desirably select wavelengths of 190-230 nm from the light. The photomultiplier 36 is arranged to detect the fluorescence of the excited substance laterally emitted from the fluorescent chamber through similar filters 42', 42" and a lens 41'.

The instrument in the first embodiment of the invention is constructed as hereinabove. Thus, the zero gas or span gas introduced into the measuring conduit 20 through the cocks 16 and 18 or the sample gas introduced into the same conduit 20 is supplied with pure oxygen or air from the oxygen compensation line 33, thereby making it possible to attain a desired $O_2$ concentration which brings the background to a stable low value. The permeation wet remover 21 is capable of removing the moisture molecules from the gas therethrough by permeating them into the vacuum channel 32 without condensation, with no loss caused by any dissolution of $SO_2$ into condensed phase. The moisture-removed gas is passed through the capillary 22 to the cutter 23, where it is to remove any aromatic hydrocarbons therein which are major components interfering with $SO_2$ fluorimetry, and thence it is fed to the fluorescent chamber 24.

In the flow system described above, by selecting the flow resistances of the oxygen compensation line 33 and measuring conduit 20 at a desired rate, it is possible to allow air or pure oxygen to meet the gas in the measuring conduit 20, always at a fixed ratio, to provide a stable low background value.

It will be recalled that the $O_2$ concentration-background characteristic studied in preparing the first embodiment has changed sharply for the worse to unstable low levels at the region where the $O_2$ concentration is less than about 1-2%, as shown in FIG. 1. This means that when the oxygen introduced into the fluorescent chamber as irradiated by ultraviolet rays at the range of 190-230 mm, occupies a concentration up to about 1-2% in gaseous phase, it is so effectively excited that the background may be substantially suppressed. While the suppressed background in a stable low level would no longer decay on the saturation of suppression with $O_2$ in such a concentration, I have hypothesized that such effective excitation of oxygen is due to the formation of $O_3$ through the decomposition (O*) of $O_2$ and also keeping the ozone atmosphere itself at a substantial balanced concentration.

On this hypothesis, it follows that among the zero gas components, what contributes to the base stabilization and plays an important role is $O_3$ rather than $O_2$ itself. In order to confirm this, I have measured background values associated with zero gases composed of an $O_2$-+$O_3$+$N_2$ system which initially contain 200-450 ppm $O_3$.

Referring to FIG. 4, the result of this measurement is shown. The curve A is a reproduction of the $O_2$ background curve shown in FIG. 1, whereas the curve B is a background curve obtained by passing oxygen or air through an ozonizer to provide an $O_2$ concentration equal to that of A and an $O_3$ concentration of 200-450 ppm. approximately proportional thereto. A comparison between the curves A and B shows that the base provided by substantially introducing $O_2$ into the fluorescent chamber through the ozonizer is stabilized at a much lower level than when $O_2$ alone is introduced and that the variations in its base curve would be negligible for $O_3$ concentrations (which are above about 250 ppm, as will be later described) corresponding to $O_2$ concentrations of above about 0.5%. Thus, it has been confirmed that $O_3$ plays a major role in stabilizing the base.

A second embodiment of the invention is intended to provide a fluorometric $SO_2$ measuring technique wherein the measuring base is stabilized by adding $O_3$ to a sample gas and a reference gas.

Figure 5:
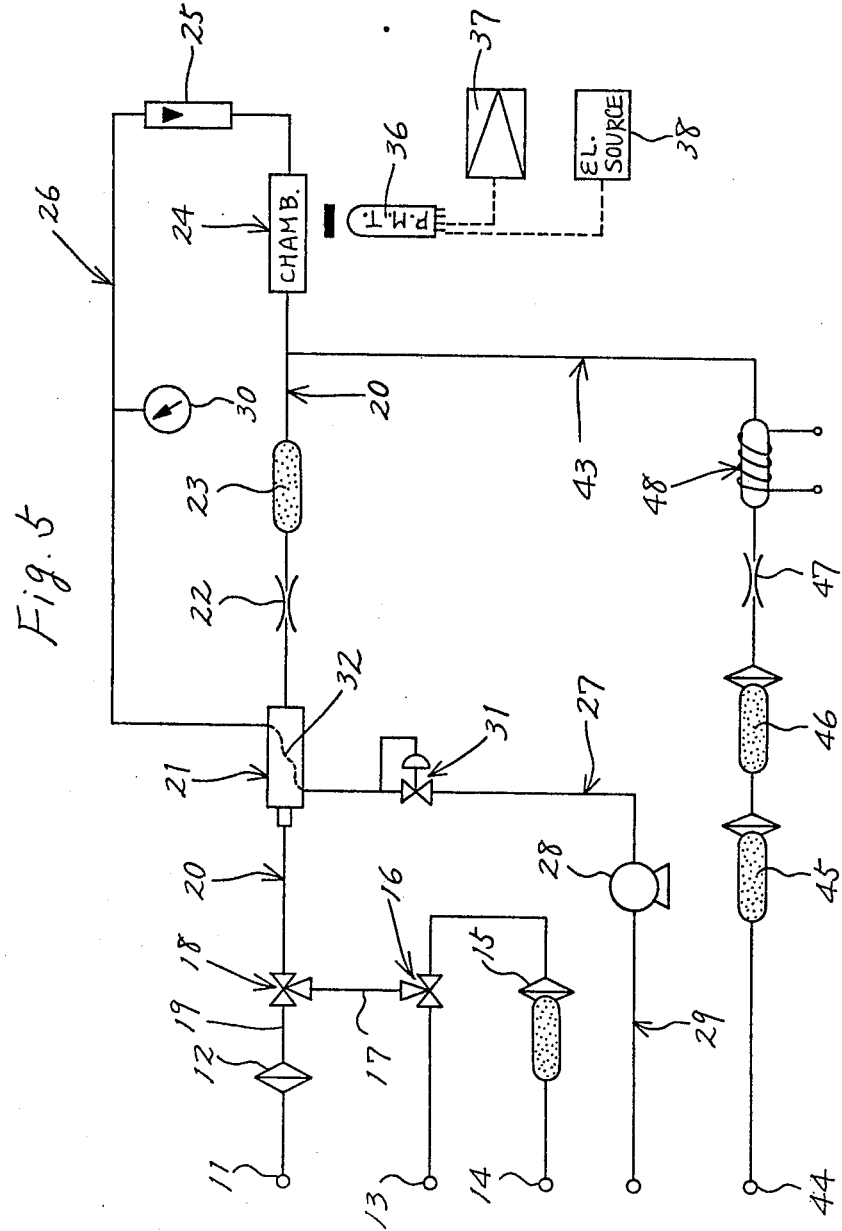
FIG. 5 is a diagram showing the flow outline of an embodiment of the invention employing a flow system for supplying the reference gas with $O_3$.

Referring to FIG. 5, a flow system for embodying the method of the invention is shown. In this embodiment, the flow system starting at a sample gas inlet 11, span gas inlet 13 and zero gas inlet 14, extending through a fluorescent chamber 24 and vacuum conduits 26, 27 to an exhaust conduit 29, is the same as the flow system shown in FIG. 2, except that the oxygen compensation line is replaced by an ozone supply system connected to the immediately upstream side of the chamber. Therefore, all the elements corresponding to those of FIG. 2 are given the same numerals and a detailed description thereof is omitted. Further, the optical construction related to the fluorescent chamber 24, the one shown in FIG. 3 is also employed in the second embodiment.

According to the second embodiment, the outlet of an ozone supply system 43 is coupled to the measuring conduit 20 on the inlet side of the fluorescent chamber 24. The supply system 43 is so arranged that air taken in through the air inlet 44 is subjected to the removal of its dust and moisture through an activated carbon filter 45, a silica gel filter 46 and a capillary 47 and is then admitted to an ozonizer 48 so as to mix each of the zero gas or the like and the sample gas with $O_3$ at a desired ratio according to the invention, whereupon the mixture can be fed to the fluorescent chamber 24.

The instrument in the second embodiment of the invention is constructed in the manner described above. Thus, the zero gas or span gas introduced into the measuring conduit 20 through the cocks 16 and 18 or the sample gas introduced into the measuring conduit 20 through the cock 18 is supplied with $O_3$-containing air from the supply system 43 at the upstream side of the fluorescent chamber 24, whereby a desired $O_3$ concentration which brings the background to a stable low value can be attained. The permeation wet remover 21 is capable of removing the moisture in the molecular state from the gas by permeation without condensing it, in the same manner as the first embodiment, with no loss caused by the dissolution of $SO_2$. Similarly, the moisture-free gas is passed through the capillary 22 to the cutter 23 where it is subjected to the removal of its aromatic hydrocarbons which are considered as major components interfering with $SO_2$ fluorimetry, whereupon it is fed to the fluorescent chamber 24.

In the second embodiment described above, by setting the flow resistances of the $O_3$ supply conduit 43 and measuring conduit 20 at a desired ratio, it is possible to allow air or pure oxygen to meet the gas in the measuring conduit 20, always at a fixed ratio, to provide an extremely stable low background value.

Figure 6:
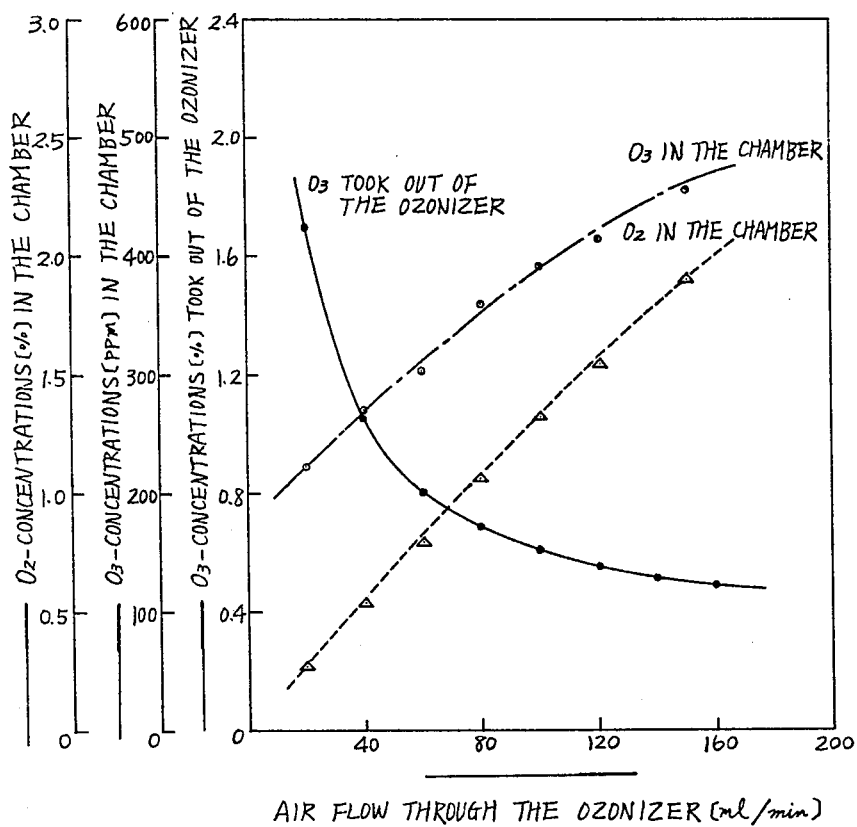
FIG. 6 is a graph showing the relationship between the air flow rate, $O_2$ concentration and $O_3$ concentration in an ozonizer and a fluorescent chamber connected thereto.

Referring to FIG. 6, where a zero gas comprising $N_2$ gas is passed through the measuring conduit at the rate of 1.5 l/min while the flow rate of air flowing into the ozone supply system is 20–200 ml/min, the graph shows the generated ozone concentration (%) at the ozonizer 48, and the relationship between the ozone concentration (ppm) arriving at the fluorescent chamber 24 and the oxygen concentration inside the fluorescent chamber 24. According to these curves, it is seen that as the air flow rate increases, the generated ozone concentration decreases to a certain extent but the ozone concentration inside the fluorescent chamber 24 increases in approximate proportion to the air flow rate till about 450 ppm, it being clear that a preferable base value in the range shown in FIG. 4 can be set. In the embodiment, when the flow rates of the sample and reference gases are 1 l/min, the ozonizer air flow rate is 70 ml/min and hence the $O_3$ concentration is 350 ppm. However, as described above with reference to FIG. 4, an ozonizer-air flow rate of about 40 ml/min is sufficient to provide an $O_3$ concentration of 250 ppm.

As described so far, the present invention provides a preferable method and instrument for fluorometrically determining the $SO_2$ concentration of a sample gas. In the illustrated embodiments, the pulse fluorimetry has been described. However, the invention is, of course, applicable also in the case of irradiation with non-pulse light.

What is claimed is:

1. A method of fluorometrically determining the $SO_2$ concentration in a sample gas by irradiating said sample gas with ultraviolet rays in an absorption range by $SO_2$ molecules and measuring the intensity of luminescence of the sample gas caused thereby, said method comprising the steps of:
   (i) adding an $O_2$-supplying gas to a reference gas to increase its $O_2$ concentration to at least above about 2%, and
   (ii) measuring the light intensity from the $O_2$-supplied reference gas under the same conditions as said sample gas as the value corresponding to a zero or spanned value.

2. A method as set forth in claim 1, wherein the wavelength range of the ultraviolet rays is about 190–230 nm.

3. A method as set forth in claim 1, wherein said $O_2$-supplying gas consists of substantially pure oxygen.

4. A method as set forth in claim 1, wherein said $O_2$-supplying gas consists of air.

5. A method as set forth in claim 1, wherein said sample gas is supplied with said $O_2$-supplying gas to an $O_2$ content of more than 2%.

6. A method as set forth in claim 5, wherein the supply of $O_2$ to the sample gas is effected by using pure oxygen.

7. A method as set forth in claim 5, wherein the supply of $O_2$ to the sample gas is effected by using air.

8. A method as set forth in claim 1, wherein the zero gas component of the reference gas is $N_2$.

9. A method as set forth in claim 1, wherein the ultraviolet rays used to irradiate the sample gas and reference gas are pulse-lighted.

10. A method of fluorometrically determining the $SO_2$ concentration in a sample gas by irradiating said sample gas with ultraviolet rays in an absorption range and measuring the intensity of the luminescence of the sample gas caused thereby, said method comprising the steps of:
    (i) adding $O_3$ gas to a reference gas to indicate a reference value corresponding to the zero or spanned value for $SO_2$ concentration, and
    (ii) thereafter measuring the light intensities of said sample and reference gases as said reference value and the sample-measured value.

11. A method as set forth in claim 10, wherein the $O_3$ concentration within the fluorescent chamber is at least about 250 ppm.

12. A method as set forth in claim 10 wherein the zero gas component of the reference gas is $N_2$.

13. A method as set forth in claim 10, wherein the wavelength range of the ultraviolet rays incident into the fluorescent chamber is about 190–230 nm.

14. A method as set forth in claim 10, wherein the ultraviolet rays used to irradiate the sample gas and reference gas are pulse-lighted.

15. An instrument for fluorometrically determining $SO_2$ concentration, comprising:
    a sample gas conduit means, a reference gas conduit means for flowing a reference gas therethrough to give the zero or span base of measuring, a measuring conduit means connecting both said sample and reference gas conduit means to a fluorescent chamber, said chamber being associated with an ultra violet ray source and a fluorescence detector and an ozone supply system connected to introduce an ozone gas component to said measuring conduit means.

16. An instrument as set forth in claim 15, wherein said ozone supply system comprises a channel for introduction of $O_3$ extending from an air inlet to an ozonizer at least through a filter, the outlet of said ozonizer being directly connected to said measuring conduit at a place short of said fluorescent chamber.

* * * * *